United States Patent
Smit et al.

(10) Patent No.: US 12,161,442 B2
(45) Date of Patent: Dec. 10, 2024

(54) METHOD FOR PRODUCING AN AUGMENTED PHYSIOLOGICAL SIGNAL BASED ON A MEASUREMENT OF ACTIVITY

(71) Applicant: Covidien LP, Mansfield, MA (US)

(72) Inventors: Philip C. Smit, Hamilton (GB); Paul S. Addison, Edinburgh (GB)

(73) Assignee: COVIDIEN LP, Mansfield, MA (US)

( * ) Notice: Subject to any disclaimer, the term of this patent is extended or adjusted under 35 U.S.C. 154(b) by 444 days.

(21) Appl. No.: 17/025,750

(22) Filed: Sep. 18, 2020

(65) Prior Publication Data

US 2022/0087539 A1    Mar. 24, 2022

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/1118* (2013.01); *A61B 5/1128* (2013.01);
(Continued)

(58) Field of Classification Search
CPC ... A61B 5/0205; A61B 5/1118; A61B 5/1128; A61B 5/726; A61B 5/742; A61B 5/021;
(Continued)

(56) References Cited

U.S. PATENT DOCUMENTS

| 5,891,044 A | 4/1999 | Golosarsky et al. |
| 6,224,553 B1 | 5/2001 | Nevo |

(Continued)

FOREIGN PATENT DOCUMENTS

| DE | 102008062446 A1 | 6/2010 |
| EP | 3378386 A1 | 9/2018 |

(Continued)

OTHER PUBLICATIONS

Addison et al., "Running Wavelet Archetype Aids the Determination of Heart Rate from the Video Photoplethysmogram during Motion", 2017 39th Annual International Conference of the IEEE Engineering in Medicine and Biology Society, Jul. 11, 2017, pp. 734-737.

(Continued)

*Primary Examiner* — Sean A Frith
(74) *Attorney, Agent, or Firm* — Fletcher Yoder, P.C.

(57) ABSTRACT

According to an aspect, a method for determining an augmented vital sign, such as heart rate or heart rate variability, includes obtaining signals from a patient when the patient is both active and inactive. An activity signal is generated from the first signal, and a physiological signal is generated from the second signal. An activity weight factor is calculated from the activity signal, and a vital sign signal is calculated from the physiological signal. A mapping from the activity signal to the vital sign aids the determination of the vital sign through a motion period. The augmented vital sign is a result of the combination of first and second values, including the product of the activity weight factor and an activity derived vital sign, and the product of the vital sign signal and the activity weight factor less than one.

20 Claims, 10 Drawing Sheets

(51) Int. Cl.
*A61B 5/021* (2006.01)
*A61B 5/024* (2006.01)
*A61B 5/0245* (2006.01)
*A61B 5/11* (2006.01)

(52) U.S. Cl.
CPC ............. *A61B 5/726* (2013.01); *A61B 5/742* (2013.01); *A61B 5/021* (2013.01); *A61B 5/02405* (2013.01); *A61B 5/02427* (2013.01); *A61B 5/0245* (2013.01); *A61B 2562/0219* (2013.01)

(58) Field of Classification Search
CPC ............ A61B 5/02405; A61B 5/02427; A61B 5/0245; A61B 2562/0219
See application file for complete search history.

(56) References Cited

U.S. PATENT DOCUMENTS

| | | | |
|---|---|---|---|
| 6,532,382 | B2 | 3/2003 | Meier et al. |
| 7,860,560 | B2 | 12/2010 | Beise |
| 8,060,190 | B2 | 11/2011 | Sornmo et al. |
| 8,983,603 | B2 | 3/2015 | Perschbacher et al. |
| 10,016,141 | B2 | 7/2018 | Levitan et al. |
| 10,058,253 | B2 | 8/2018 | Parton et al. |
| 10,405,761 | B2 | 9/2019 | Ouwerkerk et al. |
| 10,420,527 | B2 | 9/2019 | Misra et al. |
| 2003/0181815 | A1 | 9/2003 | Ebner et al. |
| 2010/0013642 | A1* | 1/2010 | Watson ................... G16Z 99/00 340/573.1 |
| 2010/0174205 | A1 | 7/2010 | Wegerif |
| 2014/0275832 | A1 | 9/2014 | Muehlsteff et al. |
| 2015/0208931 | A1 | 7/2015 | Kasamsook et al. |
| 2016/0007935 | A1* | 1/2016 | Hernandez ............. A61B 5/024 600/595 |
| 2016/0256060 | A1 | 9/2016 | Katra |
| 2018/0279885 | A1* | 10/2018 | Bulut ................... A61B 5/7221 |
| 2018/0303357 | A1 | 10/2018 | Galeev et al. |
| 2022/0061685 | A1 | 3/2022 | Addison |

FOREIGN PATENT DOCUMENTS

| | | | |
|---|---|---|---|
| KR | 20060031837 | A | 4/2006 |
| KR | 100745972 | B1 | 7/2007 |

OTHER PUBLICATIONS

International Search Report for International Application No. PCT/US2021/047233; Application Filing Date: Aug. 24, 2021; Date of Mailing: Nov. 16, 2021; 5 pages.

International Search Report for International Application No. PCT/US2021/050378; Application Filing Date: Sep. 15, 2021; Date of Mailing: Jan. 4, 2022; 4 pages.

Written Opinion for International Application No. PCT/US2021/047233; Application Filing Date: Aug. 24, 2021; Date of Mailing: Nov. 16, 2021; 19 pages.

Written Opinion for International Application No. PCT/US2021050378; Application Filing Date: Sep. 15, 2021; Date of Mailing: Jan. 4, 2022; 8 pages.

Lindberg, S., "What Can RPE Tells Us About Exercise?" Healthline, Mar. 8, 2019, 6 pages.

* cited by examiner

METHOD FOR PRODUCING AN AUGMENTED PHYSIOLOGICAL SIGNAL BASED ON A MEASUREMENT OF ACTIVITY

FIELD

The disclosure relates to a method for producing an augmented or enhanced physiological signal based on a measurement of activity. The method may be used for augmenting or enhancing a physiological signal such as heart rate, heart rate variability, respiration rate, tidal volume, minute volume, blood pressure, oxygen saturation, perfusion index, and early warning scores, etc. Heart rate and heart rate variability may be predicted for use with a patient where the estimate of the heart rate is augmented during periods of patient activity.

BACKGROUND

Heart rate variability (HRV) metrics have shown good correlation with a disease state or stress of a patient. In a healthy individual, HRV should increase during relaxing activities and decrease during stress. HRV tends to be higher when the heart is beating slowly and lower when the heart is beating quickly (e.g., exercise, stress). While the HRV level may naturally fluctuate from day to day based on activity level and/or stress level, when an individual is in a disease state or under stress, low HRV may persist.

By monitoring HRV, patients at an elevated risk of cardiac arrhythmia or death may be identified. For example, HRV has been used to detect sepsis and the onset of sepsis in neonates, as well as other conditions, such as encephalopathy and the identification of pain.

A photoplethysmography (PPG) sensor is used to monitor HRV. PPG is the measurement of artery volume using light. When light emitted by the monitor enters the skin of a patient, most of the light is absorbed by body tissues, but some of the light is reflected. The amount of light that is reflected depends on several factors, one being the volume of arteries near the surface of the user's skin. Blood in the arteries absorbs light better than the surrounding body tissues, so as arteries contract and swell in response to the pulsating blood pressure, the intensity of the reflected light rises and falls. PPG devices detect this variation in reflected light and use the variation to estimate heart rate (HR).

There can be difficulty in accurately estimating HR and HRV when there is motion interference. Motion interference may cause signal deterioration, which in turn, causes a degradation in physiological parameters derived from the signal such as HR or HRV. Often, the motion interference and heart rate signals overlap such that it is difficult to separate the two signals. In order to reduce the chances of incorrect physiological readings, such as heart rate or heart rate variability, for example, a common strategy is to stop recording when high levels of motion interference are detected. Unfortunately, this means that during periods of increased activity, there might be a failure to record any data.

Therefore, a need exists for determining a more accurate representation of the measured heart rate and the measured heart rate variability that accounts for activity of a patient than conventional measurement techniques.

SUMMARY

According to an embodiment, a method of determining an augmented heart rate includes obtaining a video signal from a patient monitoring device; and using the video signal to generate an activity signal and to generate a video PPG. The method further includes calculating an activity weight factor from the activity signal and calculating a video PPG heart rate from the video PPG; calculating a first value from the product of the activity weight factor and an activity heart rate; calculating a second value from the product of the video PPG heart rate and a difference between one and the activity weight factor; and computing the augmented heart rate by combining the first value and the second value.

According to another embodiment, a method of determining an augmented heart rate, the method includes obtaining a first signal and a second signal from a patient; generating an activity signal from the first signal; and generating a video PPG from the second signal. The method further includes calculating an activity weight factor from the activity signal; calculating a video PPG heart rate from the video PPG; calculating a first value from the product of the activity weight factor and an activity heart rate; calculating a second value from the product of the video PPG heart rate and a difference between one and the activity weight factor; and computing the augmented heart rate by combining the first value and the second value.

According to another embodiment, a method of determining an augmented heart rate variability, includes the steps of obtaining a first signal and a second signal from a patient monitoring device; generating an activity signal from the first signal; and generating a video PPG from the second signal; and calculating an activity weight factor from the activity signal. The method further includes calculating a video PPG heart rate variability from the video PPG; calculating a first value from the product of the activity weight factor and an activity heart rate variability; calculating a second value from the product of the video PPG heart rate variability a difference between one and the activity weight factor; and computing the augmented heart rate variability by combining the first value and the second value.

According to another embodiment, a method of determining an augmented vital sign includes the steps of obtaining a first signal and a second signal from a patient; generating an activity signal from the first signal; generating a physiological signal from the second signal; and calculating an activity weight factor from the activity signal. The method further includes calculating a vital sign signal from the physiological signal; and computing the augmented vital sign by combining a first value and a second value, wherein the first value is the product of the activity weight factor and a vital sign activity level and the second value is the product of the vital sign signal and the activity weight factor less than one.

These and other features of the methods of the subject disclosure will become more readily apparent to those skilled in the art from the following detailed description of the preferred embodiments taken in conjunction with the drawings.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed method is presented herein by way of exemplification and not limitation with reference to the Figures.

A heart rate (HR) is derived from an activity signal which may be used to augment a video PPG signal during motion. The method may be used to determine both a heart rate and a heart rate variability measure during periods where the underlying physiological signal is poor. Thus, when a neonate is inactive, an accurate PPG video heart rate can be acquired. To the contrary, when the neonate is moving, the heart rate is estimated through a degree or amount of activity, i.e., the amount of movement is directly related to the heart rate. Moreover, the PPG video heart rate is fused or combined with the activity heart rate through a weighted combination of the two heart rate sources. Ultimately, this results in an augmented heart rate.

Figure 1A:
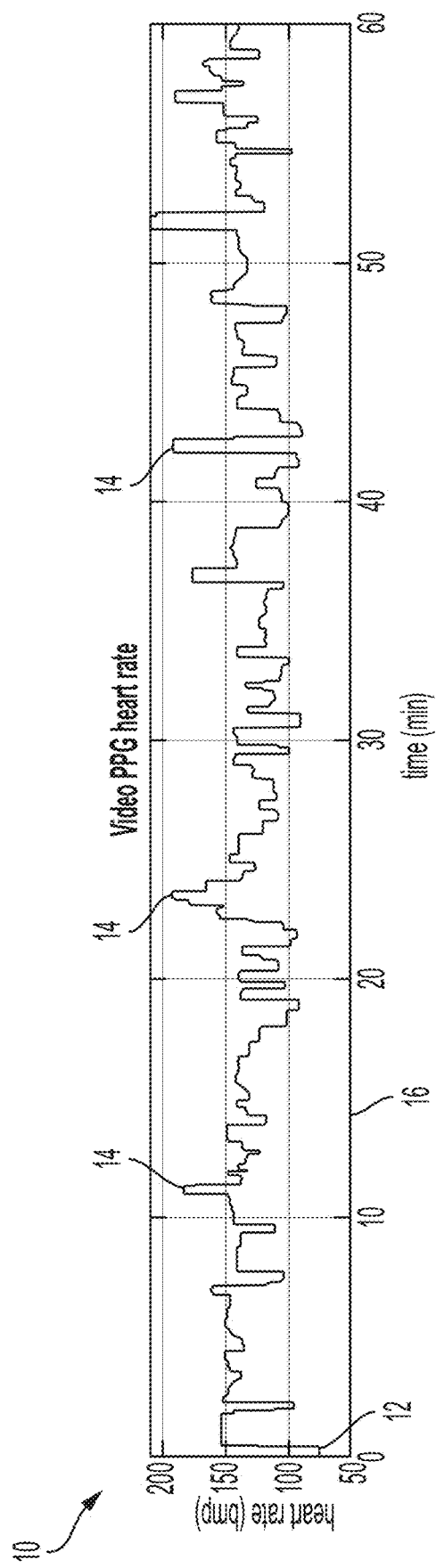
FIGS. 1a and 1b depict plots of a heart rate from a video PPG and a heart rate from an ECG reference signal according to conventional techniques.
Figure 1B:
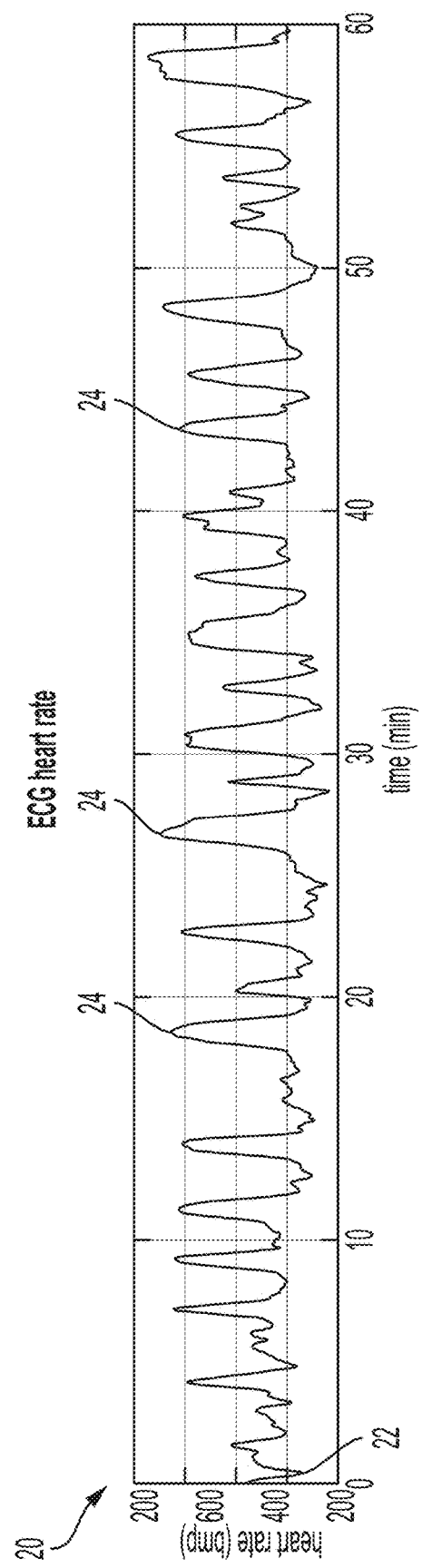

As seen in FIG. 1a, a plot 10 shows a heart rate measurement 12 from a video PPG as acquired from a neonate. The plot 10 was generated when the neonate moved frequently during the observation period. The effect of motion may be seen in the plot 10, as represented by multiple peaks 14 over the time period 16. The plot 20 shown in FIG. 1b is the heart rate measurement 22 derived from a source such as an ECG reference signal, which includes intermittent excursions 24 in a heart rate around 140 bpm and 180 bpm, which are expected. The heart rate measurement 22 may also be derived from other sources such as a pulse oximeter signal, a blood pressure signal, a heart sound signal, etc. that is considered accurate for clinical heart rate measurements. As seen when comparing the data shown in FIG. 1a with that shown in FIG. 1b, the motion of the neonate has significantly degraded the heart rate measurement 12 from the video PPG signal. Consequently, there is little correlation between the ECG heart rate of FIG. 1b and the video PPG heart rate of FIG. 1a.

Figure 2:
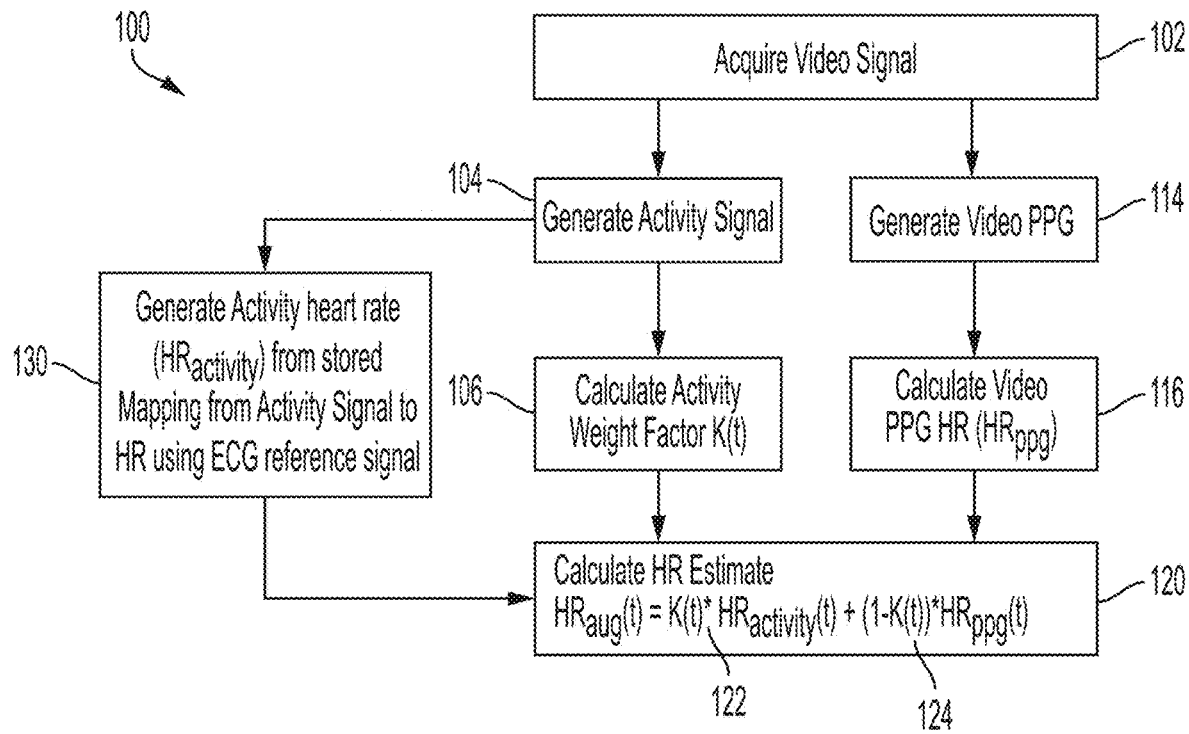
FIG. 2 depicts a flowchart of a method according to an exemplary embodiment where a video signal is acquired to calculate an augmented heart rate.

According to one embodiment, as seen in FIG. 2, a method 100 of determining an augmented heart rate HRaug 120 of a patient includes the step of obtaining or acquiring a video signal 102 from the patient. The video signal 102 is a stream of still images that may include, but is not limited to, RGB, depth, infrared, thermal, and radio wave data (e.g., milli-wave), etc., or any combination of these signals. The video signal 102 is then used to generate an activity signal 104 and also to generate a video PPG signal 114. Both the activity signal 104 and the video PPG signal 114 are continuously calculated. The activity signal 104 is generated all of the time such that it is possible to monitor the amount of activity present at any point, even in instances when there is no activity. Similarly, the video PPG signal 114 is generated all of the time, even in instances when there is an increased amount of activity such that there is an unfavorable signal.

A heart rate signal may be generated from a physiological monitoring device. As seen in FIG. 2, this is a heart rate signal generated from a non-contact camera (HRppg) 116. This may be done using color changes on the skin of the patient and/or small fluctuations due to ballistocardiographic effects.

As seen in FIG. 2, the acquired video signal 102 is also used to generate an activity signal 104. In the method 100, the activity heart rate signals may be derived from one or more different signals. The one or more different signals may be from at least one or more of an RGB video signal, a depth camera signal, an accelerometer signal, a piezoelectric motion signal, a PPG, an ECG, a blood pressure signal, etc., or a combination of these signals.

The activity signal 104 is further used to generate an activity heart rate HRactivity 130. This is done by mapping the activity signal to a reference signal using a predefined relationship, which will be discussed below and with reference to FIGS. 4 and 5. When there is motion on the signal that is being monitored, the mapping aids the determination of heart rate through the motion period. Thus, the activity heart rate 130 is generated from a stored mapping 133 from the activity signal to an ECG reference signal HRecg 108. As seen in FIG. 2, the activity signal 104 is also used to calculate an activity weight factor 106, K(t).

The activity weight factor K(t) 106 may be derived from the activity signal 104 in many ways. The activity weight factor K(t), like the activity signal 104 and the video PPG signal 114, is continuously calculated. The activity weight factor K(t) is then used to determine how much weight to assign to each of the measurements. For example, K(t) may be obtained from a relationship derived from the activity signal 104, that is a function of the amplitude of the activity signal. This function may be a function such that the activity weight value is limited between zero and one. For example, this function may be a sigmoidal function such that the activity weight value is limited between zero and one. The amplitude of the activity signal may also be limited by thresholding or any other method that will ensure the activity weight factor is between zero and one. The activity weight factor K(t) reflects the amount of activity and its effect on the signal quality.

The movements and activity of the patient are continuously monitored to determine the activity weight factor K(t). Therefore, whether the patient is active or inactive, an activity weight factor K(t) is calculated 106 and a video PPG heart rate signal HRppg 116 from the video PPG 114 is determined. Then, using both the activity weight factor K(t) 106 and the video PPG heart rate 116, an augmented heart rate 120 is calculated.

The augmented estimate is then produced by adding together the two weighted estimates, a first value 122 and a second value 124. Thus, at each time instance, the first value 122 is calculated from the product of the activity weight factor K(t) 106 and an activity heart rate 130; and the second value 124 is calculated from the product of the video PPG heart rate signal 116 and a difference between one and the activity weight factor K(t) 106. The final output heart rate HRaug 120 is determined by fusing these two heart rate measures, as shown in FIG. 2.

Moreover, a weighted average of the first value or the activity-based estimate 122 and the second value or the video-based estimate 124 is calculated. Accordingly, the first value 122 and the second value 124 are combined to compute the augmented heart rate HRaug, 120. The augmented heart rate 120 is computed using the equation:

$$HR_{aug}(t) = K(t)^* HR_{activity}(t) + (1 - K(t))^* HR_{ppg}(t).$$

Given this equation and the activity weight factor K(t), where there is no activity, the augmented heart rate HRaug is equal to the original heart rate signal from the video PPG, HRppg. When there is excessive motion, then the HRaug may be derived from the activity signal alone. Between these two extremes, the HRaug may be a combination of the original video PPG HR signal and the one generated by the activity signal. As such, when the activity signal 104 indicates that there is no activity, then only the video PPG signal 114 is used as the output. When the activity signal 104 indicates that there is activity, then the video PPG is augmented using the previously generated mapping 130 from the ECG reference signal.

Figure 3:
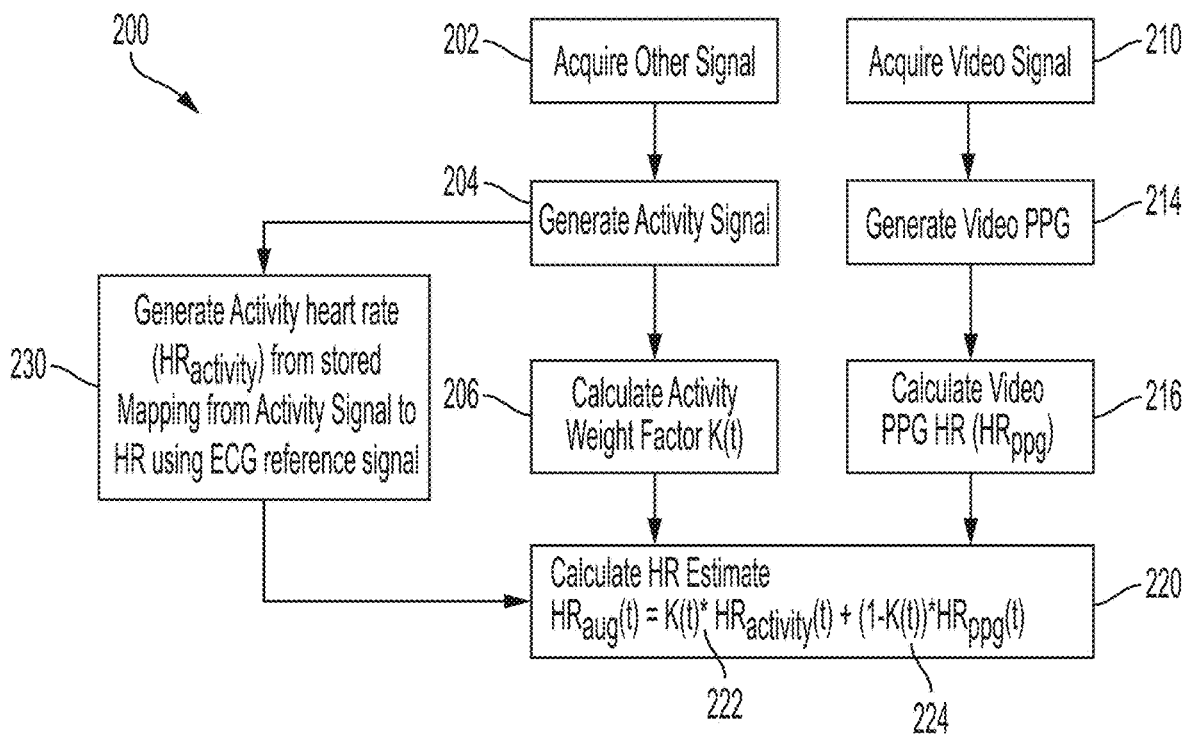
FIG. 3 depicts a flowchart of a method according to an exemplary embodiment where activity and video PPG signals are separately acquired from more than one signal to calculate an augmented heart rate.

In the method 200 shown in FIG. 3, a first signal 202 is acquired for use with an activity measurement 204 and a second separate signal or a video signal 210 is acquired for use to calculate a video PPG signal 214. With this method 200, an activity signal 204 is generated through the first signal 202 and a video PPG signal 214 is generated through different means, the video signal 210. This method 200 is also applicable where a signal other than the video PPG is used to determine a heart rate that needs to be corrected through motion, including a pulse oximeter PPG signal, for example.

As seen in FIG. 3, a first signal is acquired 202 from the patient and used to generate the activity signal 204, and a video signal is acquired 210 from the patient and used to generate a video PPG signal 214. Using the activity signal 204, the activity heart rate is generated 230 from the stored mapping from the activity signal to the ECG reference signal (described below). The mapping aids the determination of the activity heart rate as in the method described above. As with the above method 100, in the method 20 illustrated in FIG. 3, the activity weight factor K(t) is calculated 206 and together, the activity heart rate HRactivity 230 and activity weight factor K(t) 206 result in a first value 222. Furthermore, the generated video PPG signal 214 is used to calculate a video PPG heart rate HRppg 216.

Then, as with the above-described method 100, with the method 200 illustrated in FIG. 3, a second value 224 is calculated using the video PPG heart rate 226 and a deduction of one minus the activity weight factor K(t), wherein a weighted average of the first value or the activity-based estimate 222 and the second value or the video-based estimate 224 is calculated. The first value 222 and the second value 224 are combined to compute the augmented heart rate HRaug, 220. Specifically, the augmented heart rate over time 220 is computed using the equation:

$$HR_{aug}(t) = K(t)^* HR_{activity}(t) + (1 - K(t))^* HR_{ppg}(t).$$

Figure 4:
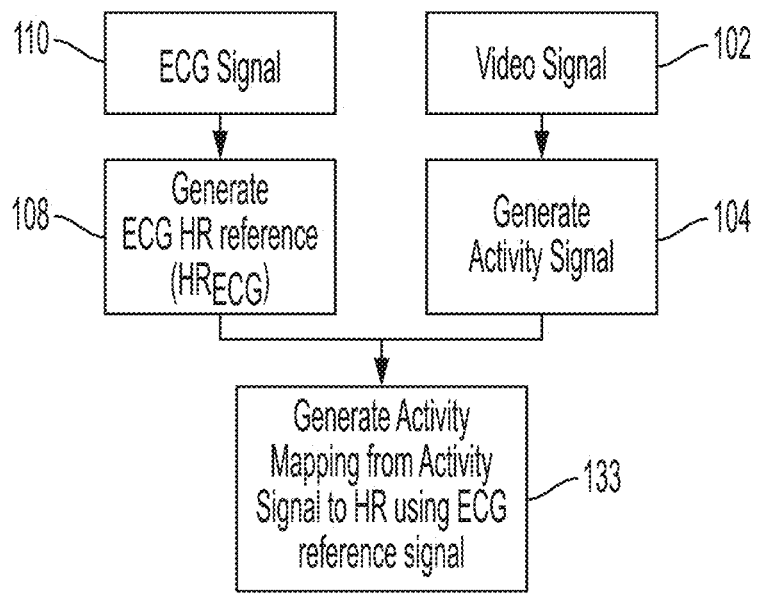
FIG. 4 depicts a flowchart for generating a mapping from an activity signal to a heart rate signal according to the exemplary embodiment shown in FIGS. 2 and 3.

Patient activity causes a change in heart rate. Generally, the more active a patient, the higher the heart rate. When there is motion on the signal that is being monitored, the mapping aids the determination of heart rate through the motion period. While there are many ways to derive a mapping from an activity signal to a heart rate signal, the general principle for generating such a mapping is shown in FIG. 4. Once the activity mapping is generated 133, the value is used to generate an activity heart rate, HRactivity 130, for example.

The flowchart depicted in FIG. 4 further elaborates on the activity mapping step 130, 230 from the corresponding methods shown in FIG. 2 and FIG. 3, wherein the activity 130, 230 is mapped onto a heart rate using a predefined relationship and ultimately, the mapping 133 is used to generate the activity heart rate. As seen in FIG. 4, the activity heart rate HRactivity 130 is calculated from a mapping 133 of the activity signal 104 and an ECG reference signal 108. The mapping 133 is generated by obtaining a reference ECG signal 108, obtaining the activity signal 104, and then generating the mapping from the activity signal 104 to the reference ECG signal 108. For this example, as shown in FIG. 5, a linear regression between an activity signal 104 and a heart rate reference from a reference ECG signal 108 provides the mapping 133.

Figure 5:
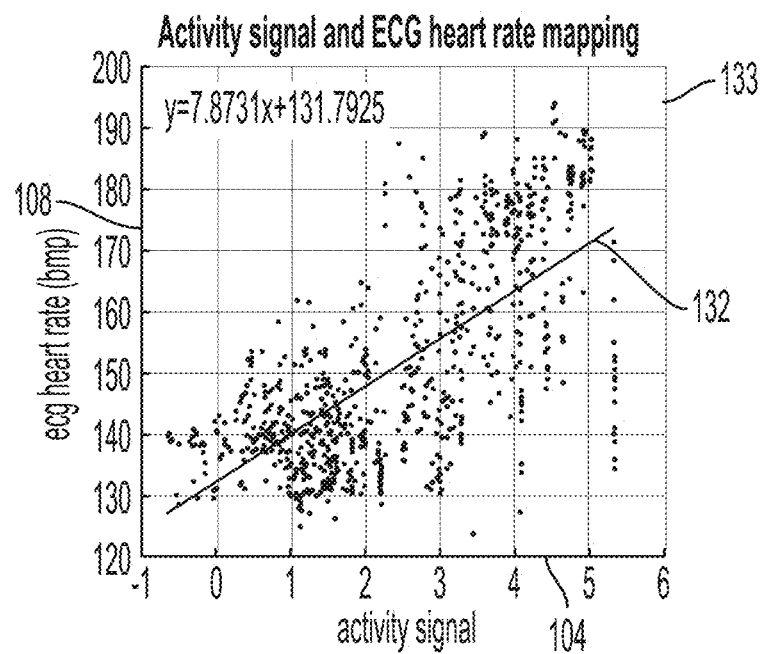
FIG. 5 depicts a graph illustrating a linear regression between an activity signal and heart rate from an ECG in accordance with FIG. 4.
Figure 6A:
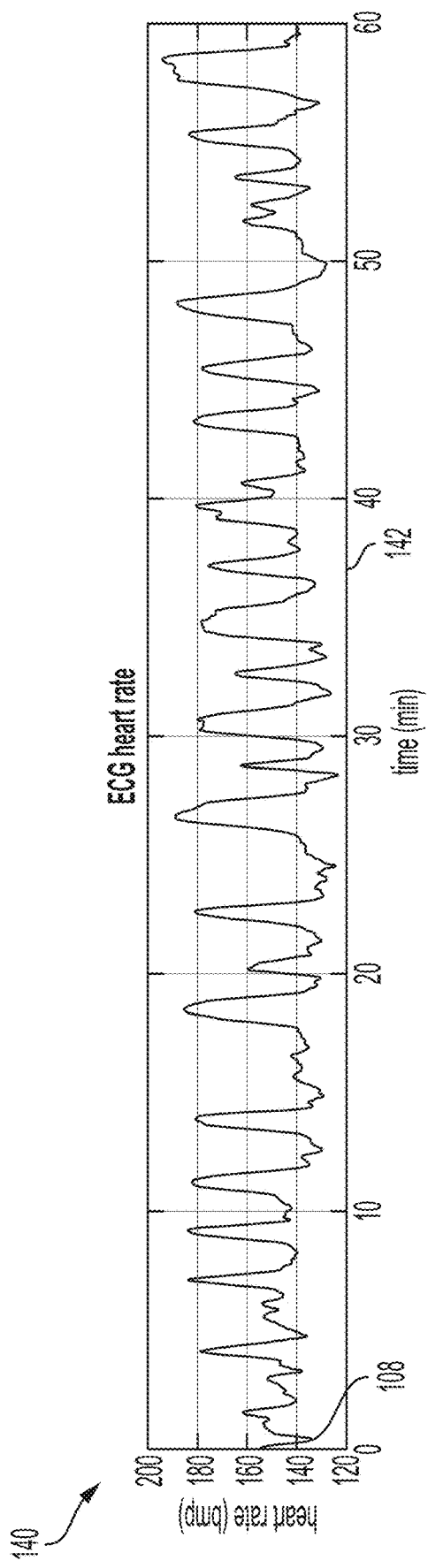
FIG. 6a depicts an ECG heart rate plot with the data from the graph of FIG. 5 in accordance with an exemplary embodiment.
Figure 6B:
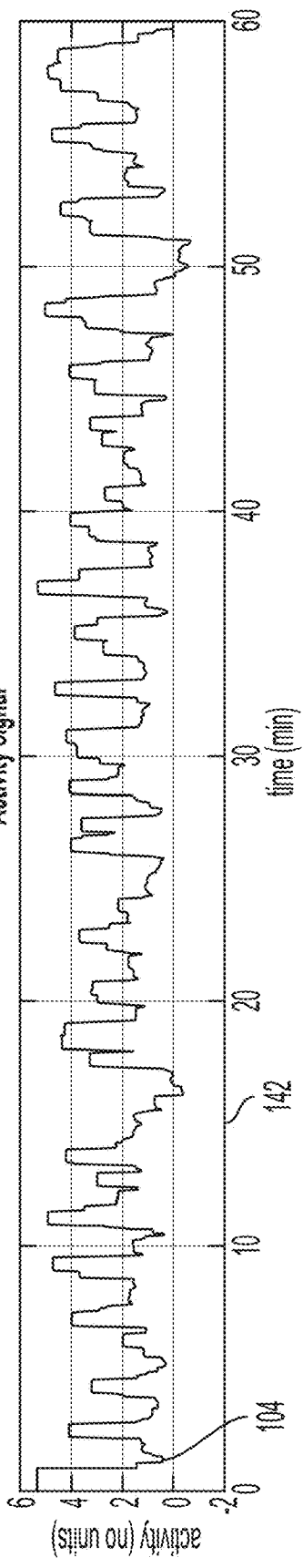
FIG. 6b depicts an activity signal plot with the data from the graph of FIG. 5 in accordance with an exemplary embodiment.

As shown in FIG. 5, a linear regression 132 between an activity signal 104 and a heart rate reference from a reference ECG signal 108 was used to provide the mapping 133 between heart rate and activity. This regression 132 is shown using data from the original signals plotted in FIGS. 6a and 6b. As shown in the plot 140 of FIG. 6a, a reference ECG signal 108 is collected over a period 142 which includes motion. As shown in the plot 144 of FIG. 6b, the corresponding activity 104 is depicted over the same time period 142. Accordingly, the linear regression 132 in FIG. 5 depicts the activity signal 104 and the reference ECG signal 108 mapping from the data collected in FIGS. 6a and 6b.

Methods other than linear regression may be used to provide a mapping between activity and heart rate. For example, a non-linear fit of the data or a parametric physiological model of activity and heart rate may be used. The mapping is ultimately used to compute the augmented HR and augmented HRV.

Figure 7A:
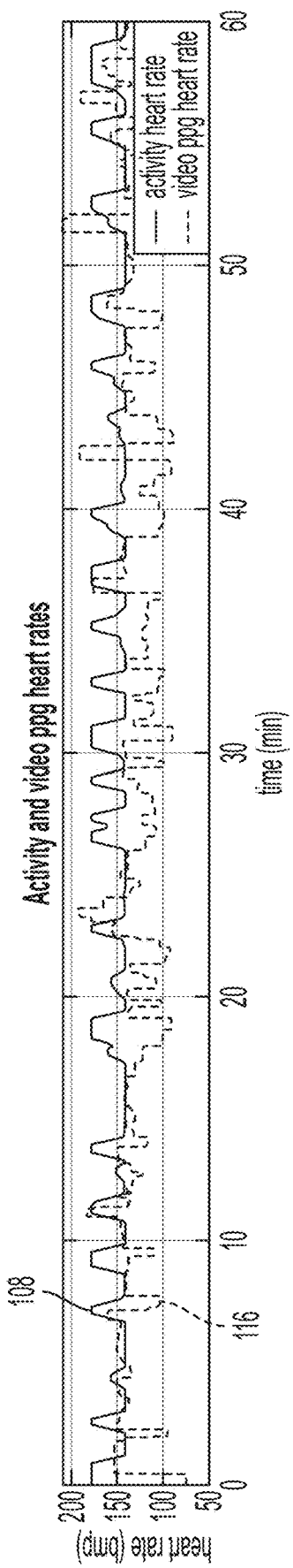
FIG. 7a-7d depict plots related to augmented heart rate and augmented heart rate variability generated from the activity heart rate in accordance with an exemplary embodiment.
Figure 7B:
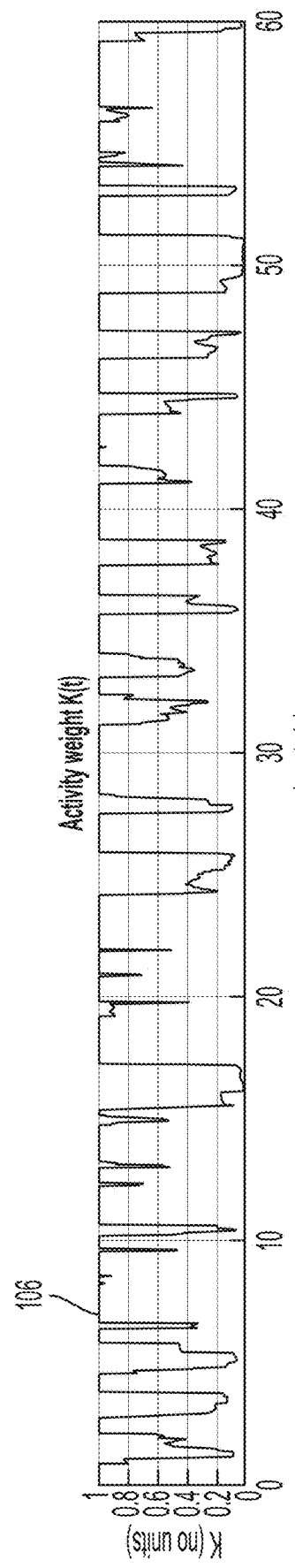
Figure 7C:
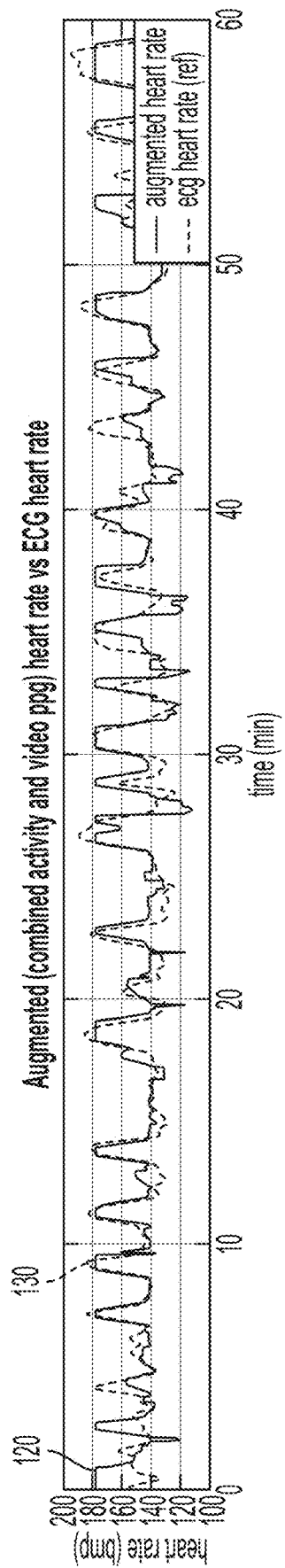
Figure 7D:
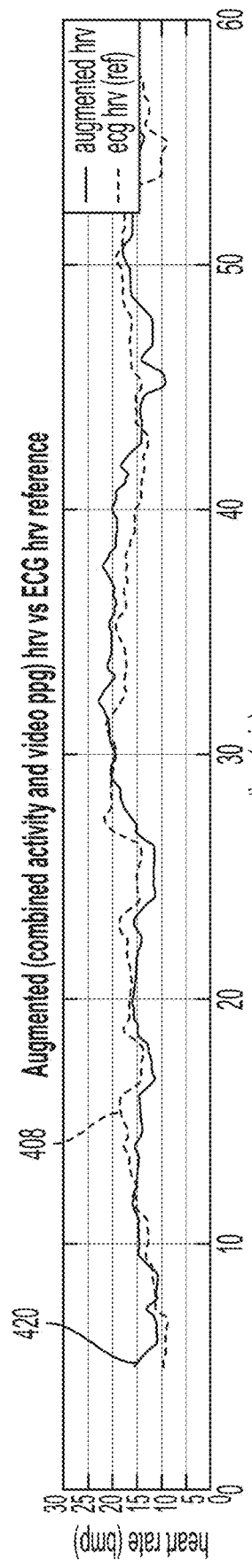

Turning to additional plots shown in FIGS. 7a-7d, augmented heart rate and augmented heart rate variability generated from the activity heart rate and activity heart rate variability, respectively, in accordance with an exemplary embodiment are depicted. As seen in FIG. 7a, the activity and video PPG heart rates are illustrated. The activity heart rate 108 derived from the activity signal 104 is illustrated as well as the video PPG heart rate signal 116. The plot shown in FIG. 7b depicts the weight function K(t) 106. FIG. 7c is a plot showing the generated HRaug 120 plotted over time. Along with this data, the reference heart rate from the ECG HRecg 130 is also shown on FIG. 7c. The plot in FIG. 7d shows the augmented HRV signal 420 generated from the HRVecg reference 408. While any measure of HRV may be used in the method, with this plot, a five-minute standard deviation of the heart rate was used as a measure of HRV.

Figure 8:
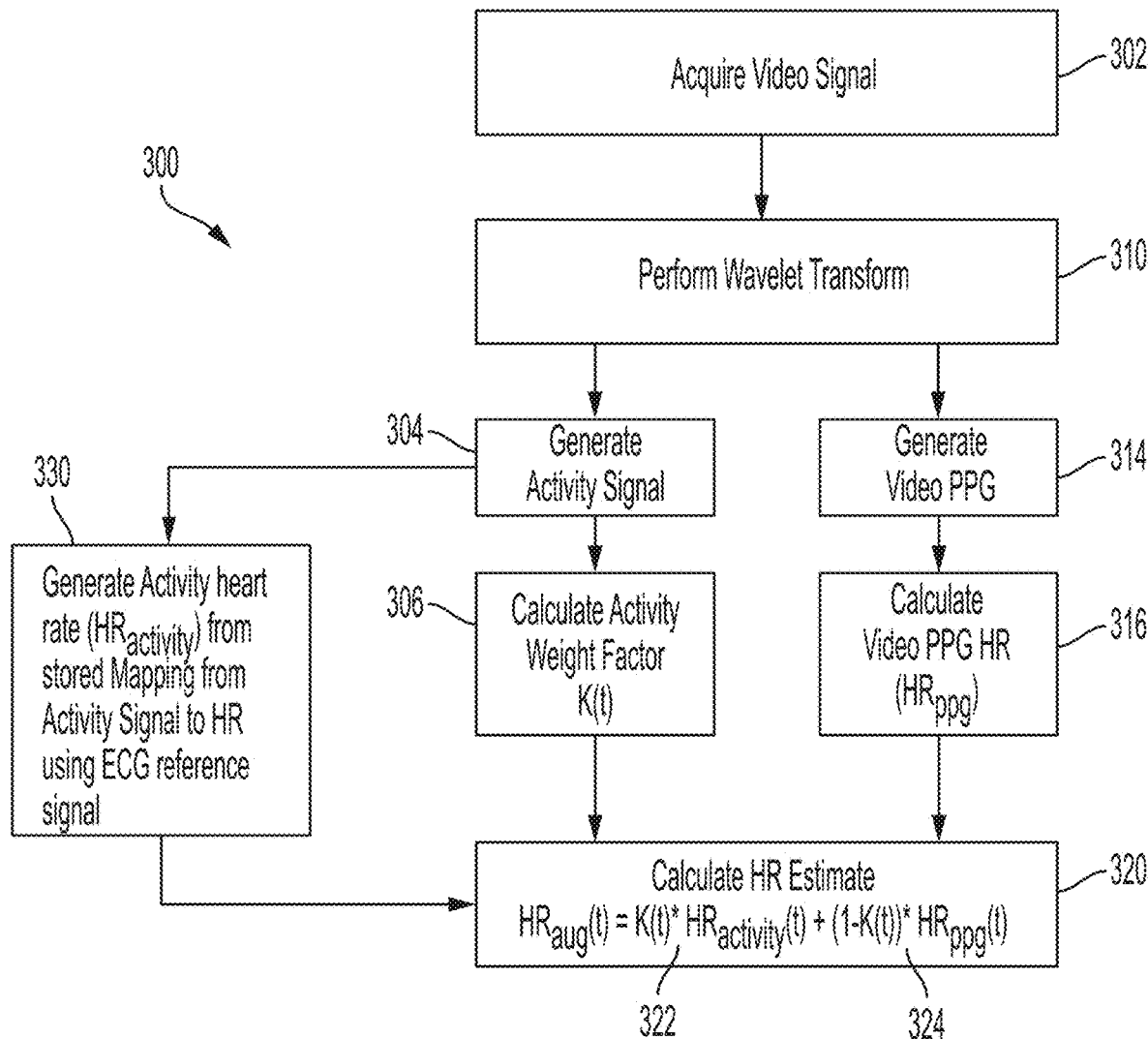
FIG. 8 depicts a flowchart of a method for acquiring a video signal and transforming the signal to calculate an augmented heart rate according to an exemplary embodiment.

In an alternative method for determining an augmented heart rate 300, as shown in FIG. 8, a video signal is acquired 302 and the incoming signal or signals 302 may be transformed 310 before calculating activity and heart rate signals. This may be a time-frequency transform such as a wavelet transform 310. The wavelet transform 310 modulus of a video PPG signal is described below and shown in FIG. 9. As seen here, the wavelet transform 310 is employed in order to extract both the activity signal 304 and heart rate data. Thus, the activity signal 304 and the video PPG signal 314 may be extracted from the wavelet transform 310. With this method 300, a video signal 302 is obtained from a patient and then converted into the time-frequency transform 310 configured to extract the activity signal 304 and the video PPG signal 314. Specifically, the wavelet transform 310 is used to generate the activity signal 304 and to generate the video PPG heart rate signal HRppg 314.

As with the methods described above, an activity weight factor K(t) is calculated 306 from the activity signal 304 and a video PPG signal HRppg 316 is calculated from the video PPG 314. Continuing, as with the above-described methods 100, 200, with the method 300 illustrated in FIG. 8, a first value 322 is calculated from the product of the activity weight factor 306 and an activity heart rate 330 generated from a stored mapping (not shown) from the activity signal 304 to a reference ECG signal (not shown), and a second value 324 is calculated from the product of the video PPG signal 316 and a difference between one and the activity weight factor 306. Again, as with the above methods, the first value 322 and the second value 324 are combined to result in the augmented heart rate HRaug 320. The augmented heart rate 320 is computed using the equation:

$$HR_{aug}(t) = K(t)^* HR_{activity}(t) + (1 - K(t))^* HR_{ppg}(t).$$

Figure 9:
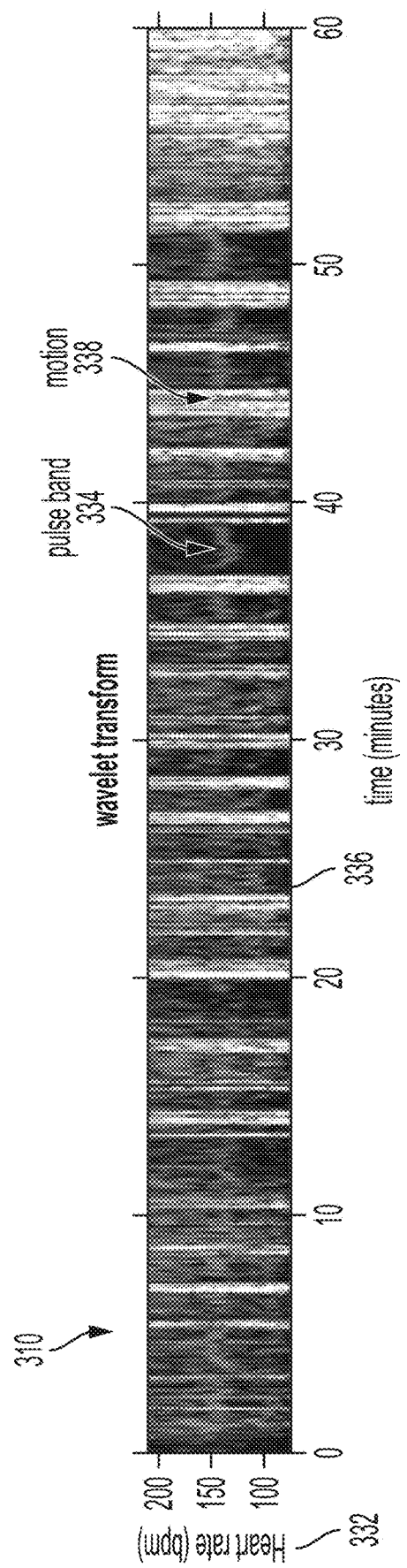
FIG. 9 depicts a wavelet transform of data extracted in accordance with the exemplary embodiment shown in FIG. 8.

As seen in the wavelet transform 310 depicted in FIG. 9, a clear heart rate signal 332 is visible during the periods that a neonate under observation is motionless. The pulse component 334 in the video PPG manifests in the wavelet modulus plot as a band across the transform plane 336. The frequency associated with this pulse band 332 at any point in time may be used to determine the instantaneous heart rate 332. Motion 338 manifests in the wavelet transform modulus 310 as distinct vertical banding over a spread of frequencies. Thus, at least one motion marker 338 is configured to be displayed as a plurality of banding over a plurality of frequencies. Thus, more activity results in higher energy content of these bands (and hence higher amplitudes) and/or longer durations of these bands and/or a wider spread of frequencies.

Figure 10:
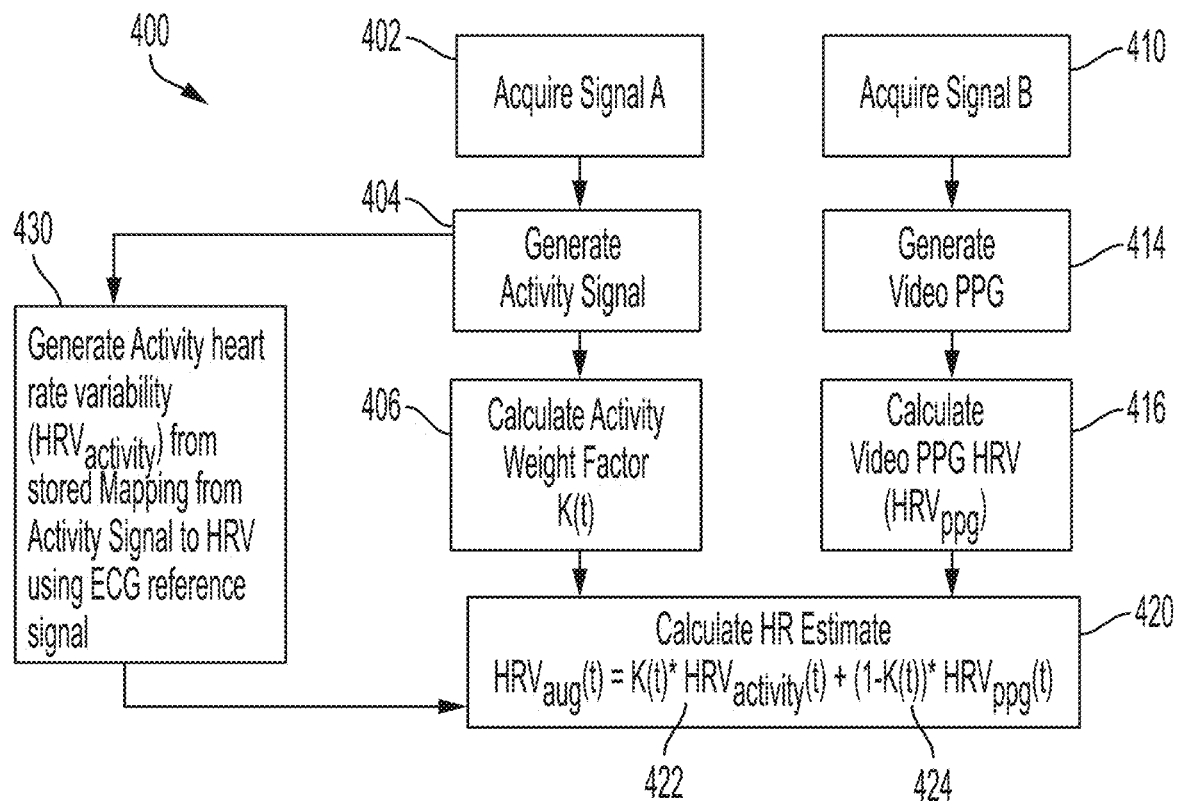
FIG. 10 depicts a flowchart of a method according to an exemplary embodiment where activity and video PPG signals are separately acquired from more than one signal to calculate an augmented heart rate variability.
Figure 11:
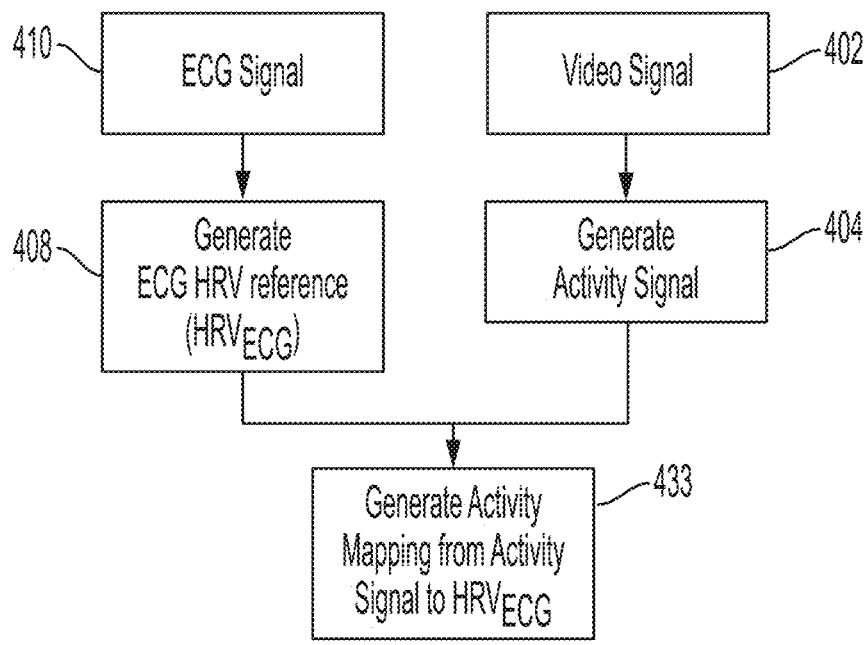
FIG. 11 depicts a flowchart for generating a mapping from an activity signal to a heart rate variability signal accordance to the exemplary embodiment shown in FIG. 10.

In another method 400, shown in FIGS. 10 and 11, similar to the methods described above, the augmented HRV, HRVaug, is computed directly using similar variables as explained in the foregoing. Similar to the above-described methods 100, 200, 300, in the method for determining an augmented HRV 400, an HRV signal 430 may be derived directly from the activity signal 404. With this method, a mapping 433 is derived between an activity signal 404 and an ECG-based HRV signal 408, as shown in FIG. 11, and then the mapping 433 is used to compute an augmented HRV directly. As seen in FIG. 10, a method of determining an augmented heart rate variability 400 includes the steps of obtaining a first signal 402 from a patient and a second signal 410 from the patient. With this method, the first signal 402 or signal A is any signal or signals which may be used to generate an activity signal 404; the second signal 410 or signal B is any signal or signals which may be used to generate a video PPG signal 414. For example, signal B could be any signal that generates a video PPG heart rate signal 416 or HRVppg. As with the above method, there is a mapping 433, shown in FIG. 11, between an activity signal 404 and a reference ECG-based HRV signal 408. The activity weight factor K(t) is calculated 406 from the activity signal 404 and the video PPG heart rate variability signal 416 is calculated from the video PPG signal 414.

The mapping 433 is generated from obtaining the reference ECG-based HRV signal 408, obtaining the activity signal 404, generating the mapping 433 from the activity signal 404 to the reference ECG-based HRV signal 408 and then used to generate the HRVactivity 430 or activity heart rate variability value. This estimate is fused with the actual HRVppg 416 which is generated in real-time from the patient. Accordingly, when there is no activity, the value of K(t) will be zero and HRVaug 420 will be the whole calculated HRVppg 416. Where there is at least some activity, such that K(t) is larger than zero, then the resulting value of HRVaug 420 depends also on HRVactivity 430 as derived from the activity to heart rate variability mapping.

Then, a first value or product 422 is calculated from the product of the activity weight factor 406 and the HRVactivity 430, and a second value or product 424 is calculated from the product of the HRVppg 416 and a difference between one and the activity weight factor 406. Then, as with the foregoing methods, the augmented heart rate 420 is calculated by combining the first product 422 with the second product 424. Thus, the augmented HRV 420 is computed using the equation:

$$HRV_{aug}(t) = K(t)^* HRV_{activity}(t) + (1 - K(t))^* HRV_{ppg}(t).$$

Figure 12:
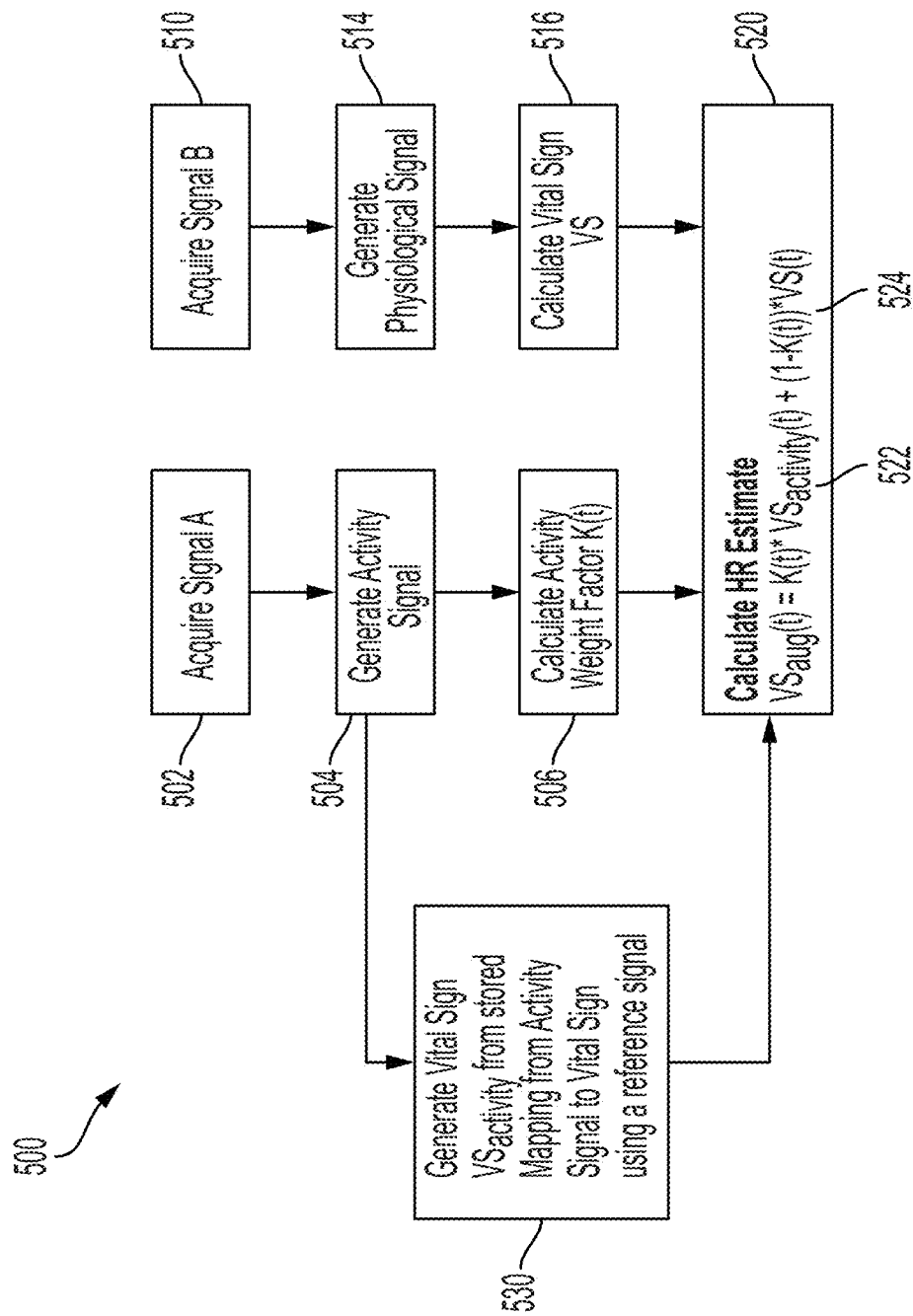
FIG. 12 depicts a flowchart of a method for determining an augmented physiological signal based on a measurement of activity in accordance with an exemplary embodiment.

The method explained in the foregoing may be generalized or applied to many other vital signs derived from acquired physiological signals. For example, the method shown in FIG. 12 may be used to generate vital signs, including respiration rate, tidal volume, minute volume, blood pressure, SpO2, perfusion index, early warning scores, etc. Turning to FIG. 12, a method of determining an augmented vital sign 500 of an individual includes the steps of obtaining a first signal 502 from a patient and a second signal 510 from a patient. With this method, the first signal 502 is any signal from the patient in order to generate an activity signal 504. The method further includes the step of obtaining a second signal 510 from the patient. The second signal 510 or signal B is any signal or signals which may be used to generate a physiological signal 514. As in the method illustrated in the above-described Figures, an activity weight factor K(t) is calculated 506 from the activity signal 504 when the patient is active.

As with the above method, there may be a mapping 530 between an activity signal 504 and a vital sign-based signal. With the vital signs as with the heart rate and heart rate variability, when there is motion on the signal that is being monitored, the mapping aids the determination of the vital sign through the motion period. A vital sign signal 516 is calculated from the physiological signal 514. Then, the augmented vital sign 520 is calculated by combining a first value or product 522 and a second value or product 524. Similar to the above-described methods, data is generated continuously using both a vital sign signal 516 and an activity weight factor 506. An augmented estimate 520 is then produced by adding the two weighted estimates, the first value 522 and the second value 524. Thus, the first value 522 is the product of the activity weight factor K(t) and a vital sign activity level 530; the second value 524 is the product of the vital sign signal 516 and the difference between one and the activity weight factor K(t). Thus, the augmented vital sign 520 is computed using the equation:

$$VS_{aug}(t) = K(t)^* VS_{activity}(t) + (1 - K(t))^* VS_{ppg}(t).$$

As with the method of determining an augmented heart rate and an augmented heart rate variability, the method of determining an augmented vital sign, includes the step of generating the vital sign activity level from a mapping from the activity signal to the vital sign signal with a reference signal. Similarly, with the mapping as it relates to a vital sign, the activity is mapped on the particular vital sign using a predefined relationship. The activity vital sign is calculated from a mapping of the activity signal and a reference signal. Patient activity causes a change in the vital sign, as with heart rate and heart rate variability. For the method depicted in FIG. 12, a regression between an activity signal and a vital sign reference provides the mapping between the vital sign and the activity.

The term "about" is intended to include the degree of error associated with measurement of the particular quantity based upon the equipment available at the time of filing the application.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of determining an augmented heart rate, the method comprising:

receiving a video signal from a camera of a patient monitoring device;
    generating an activity signal indicative of motion of a patient using the video signal;
    continuously calculating an activity weight factor as a function of an amplitude of the activity signal, the activity weight factor being indicative of an amount of the motion of the patient from the activity signal;
    determining an activity heart rate by mapping the activity signal to a reference electrocardiogram (ECG) signal;
    generating a photoplethysmography (PPG) signal from the video signal and determining a PPG heart rate from the PPG signal;
    determining the augmented heart rate by combining the activity heart rate and the PPG heart rate according to the activity weight factor; and
    displaying the augmented heart rate.

2. The method of determining the augmented heart rate of claim 1, further comprising determining the activity heart rate based on one or more different activity signals.

3. The method of determining the augmented heart rate of claim 2, wherein the one or more different activity signals comprise at least one of an RGB video signal, a depth camera signal, an accelerometer signal, a piezoelectric motion signal, a PPG, an ECG, or a blood pressure signal.

4. The method of determining the augmented heart rate according to claim 1, wherein the mapping comprises:

receiving the reference ECG signal from the patient over a period of time;
    generating the activity signal from the patient over the period of time; and
    generating a linear regression mapping from the activity signal to the reference ECG signal.

5. The method of determining the augmented heart rate according to claim 1, further including converting a stream of still images of the video signal into a time-frequency transform configured to extract the activity signal and the PPG signal, wherein each of generating the activity signal and generating the PPG signal is based on the time-frequency transform.

6. The method of determining the augmented heart rate according to claim 5, wherein the time-frequency transform is a wavelet transform.

7. The method of determining the augmented heart rate according to claim 1, wherein the activity weight factor is a function of an amplitude of the activity signal, such that the activity weight factor is limited between 0 and 1.

8. The method of determining the augmented heart rate according to claim 6, further comprising displaying the wavelet transform on at least one graph as a function of heart rate over time, such that the wavelet transform is configured to identify at least one pulse component in the PPG signal as a band across a transform plane of the wavelet transform and at least one motion marker.

9. The method of determining the augmented heart rate according to claim 8, further comprising determining an instantaneous heart rate based on a frequency associated with the at least one pulse component at a time.

10. The method of determining the augmented heart rate according to claim 8, further comprising displaying the at least one motion marker as a plurality of banding over a plurality of frequencies.

11. The method of determining the augmented heart rate according to claim 1, wherein the activity heart rate is determined based on a stored non-linear fit mapping or a parametric physiological model of activity and heart rate mapping of the activity signal to the reference ECG signal.

12. A method of determining an augmented heart rate, the method comprising:
  receiving a first signal and a second signal from a patient;
  generating an activity signal indicative of motion of the patient from the first signal;
  continuously calculating an activity weight factor as a function of an amplitude of the activity signal, the activity weight factor being indicative of an amount of the motion of the patient from the activity signal;
  determining an activity heart rate by mapping the activity signal to a reference electrocardiogram (ECG) signal;
  generating a photoplethysmography (PPG) signal from the second signal and determining a PPG heart rate from the PPG signal;
  determining the augmented heart rate by combining the activity heart rate and the PPG heart rate according to the activity weight factor; and
  displaying the augmented heart rate.

13. The method of determining the augmented heart rate according to claim 12, wherein the activity weight factor is a function of the amplitude of the activity signal, such that the activity weight factor is limited between 0 and 1.

14. The method of determining the augmented heart rate according to claim 12, further comprising generating the mapping of the activity signal and the reference ECG signal, wherein generating the mapping comprises:
  receiving the reference ECG signal from the patient over a time period;
  generating the activity signal from the patient over the time period; and
  generating a linear regression mapping from the activity signal to the reference ECG signal.

15. A method of determining an augmented heart rate variability, the method comprising:
  receiving a first signal from a patient monitoring device;
  receiving a second signal from the patient monitoring device;
  generating an activity signal indicative of motion of a patient from the first signal;
  continuously calculating an activity weight factor as a function of an amplitude of the activity signal, the activity weight factor being indicative of an amount of the motion of the patient from the activity signal;
  determining an activity heart rate variability by mapping the activity signal to a reference electrocardiogram (ECG) signal;
  generating a photoplethysmography (PPG) signal from the second signal and determining a PPG heart rate variability from the PPG signal;
  determining the augmented heart rate variability by combining the activity heart rate variability and the PPG heart rate variability according to the activity weight factor; and
  displaying the augmented heart rate variability.

16. The method of determining the augmented heart rate variability according to claim 15, further comprising generating the mapping of the activity signal and the reference ECG signal, wherein generating the mapping comprises:
  receiving the reference ECG signal from the patient over a time period;
  generating the activity signal from the patient over the time period; and
  generating a linear regression mapping from the activity signal to the reference ECG signal.

17. The method of determining the augmented heart rate according to claim 15, wherein the activity weight factor is a function of the amplitude of the activity signal, such that the activity weight factor is limited between 0 and 1.

18. A method of determining an augmented vital sign, the method comprising:
  receiving a first signal from a patient;
  receiving a second signal from the patient;
  generating an activity signal indicative of motion of the patient from the first signal;
  continuously calculating an activity weight factor as a function of an amplitude of the activity signal, the activity weight factor being indicative of an amount of the motion of the patient from the activity signal;
  determining a vital sign activity level by mapping the activity signal to a reference electrocardiogram (ECG) signal; and
  generating a physiological signal from the second signal and determining a vital sign signal from the physiological signal;
  determining the augmented vital sign by combining the vital sign activity level and the vital sign signal according to the activity weight factor; and
  displaying the augmented vital sign.

19. The method of determining the augmented vital sign according to claim 18, wherein the activity weight factor is a function of the amplitude of the activity signal, such that the activity weight factor is limited between 0 and 1.

20. The method of determining the augmented vital sign according to claim 18, further comprising generating the mapping of the activity signal and the reference ECG signal, wherein generating the mapping comprises:
  receiving a reference ECG signal;
  generating the activity signal; and
  generating the mapping from the activity signal to the reference ECG signal.

* * * * *